(12) United States Patent
Piramal et al.

(10) Patent No.: US 8,182,843 B2
(45) Date of Patent: May 22, 2012

(54) HERBAL COMPOSITIONS FOR THE TREATMENT OF DISEASES OF THE ORAL CAVITY

(75) Inventors: Swati Ajay Piramal, Mumbai (IN); Shripad Rhushikesh Jathar, Mumbai (IN); Rajesh Prabhamal Sirwani, Thane (IN); Prakash Malhotra, Mumbai (IN)

(73) Assignee: Piramal Life Sciences Limited, Mumbai (IN)

( * ) Notice: Subject to any disclaimer, the term of this patent is extended or adjusted under 35 U.S.C. 154(b) by 0 days.

(21) Appl. No.: 12/307,023

(22) PCT Filed: Jun. 29, 2007

(86) PCT No.: PCT/IB2007/052521
§ 371 (c)(1), (2), (4) Date: Dec. 30, 2008

(87) PCT Pub. No.: WO2008/001325
PCT Pub. Date: Jan. 3, 2008

(65) Prior Publication Data
US 2009/0297644 A1     Dec. 3, 2009

(30) Foreign Application Priority Data
Jun. 30, 2006 (IN) .......................... 1049/MUM/2006

(51) Int. Cl.
*A01N 65/00* (2009.01)

(52) U.S. Cl. ...................................................... 424/725
(58) Field of Classification Search .................. None
See application file for complete search history.

(56) References Cited

U.S. PATENT DOCUMENTS

| | | | |
|---|---|---|---|
| 4,780,320 A | 10/1988 | Baker | |
| 5,061,106 A | 10/1991 | Kent | |
| 5,976,506 A | 11/1999 | Vernon | |
| 6,007,795 A | 12/1999 | Masterman et al. | |
| 6,673,843 B2 | 1/2004 | Arbiser | |
| 6,833,408 B2 | 12/2004 | Sehl et al. | |
| 7,169,760 B2 * | 1/2007 | Saksena et al. | 514/3.7 |
| 2004/0120990 A1 * | 6/2004 | Cushman et al. | 424/443 |
| 2004/0185123 A1 * | 9/2004 | Mazzio et al. | 424/730 |
| 2007/0065456 A1 * | 3/2007 | Woods | 424/195.17 |

FOREIGN PATENT DOCUMENTS

| | | | |
|---|---|---|---|
| DE | 10121093 | * | 10/2002 |
| GB | 2 317 339 A | | 3/1998 |
| SU | 1132945 | | 1/1985 |

* cited by examiner

*Primary Examiner* — Michael Meller
(74) *Attorney, Agent, or Firm* — Westerman, Hattori, Daniels & Adrian, LLP

(57) ABSTRACT

The present invention relates to bioadhesive compositions for oral application, which comprise a curcuminoid substance as an active ingredient. The present invention also relates to method of using said bioadhesive composition for the prevention and treatment of periodontal diseases such as gingivitis and other periodontal diseases.

7 Claims, No Drawings

HERBAL COMPOSITIONS FOR THE TREATMENT OF DISEASES OF THE ORAL CAVITY

FIELD OF THE INVENTION

The present invention relates to a bioadhesive composition for oral application, which comprises a curcuminoid substance as an active ingredient. The present invention also relates to a method for the treatment and prevention of gingivitis and other periodontal diseases using the bioadhesive composition for oral application.

BACKGROUND AND PRIOR ART

Periodontal diseases, the diseases of oral cavity, are a group of diseases affecting the tissues surrounding the teeth. Periodontal means "around the teeth" and includes the gums and bone supporting the teeth. Gingivitis is the mildest form of periodontal (gum) disease. Gingivitis is often caused by inadequate oral hygiene, which leads to plaque buildup. As is well known, gingivitis is a general term comprising the inflammation of the gums resulting from various causes, for instance from toxic, bacterial causes, from dyscrasias, from avitaminosis etc., which are supported and promoted by salivary tartar or by other constitutional factors. The other types of periodontal diseases are aggressive periodontitis, chronic periodontitis and periodontitis associated with systemic conditions like HIV, diabetes, malnutrition and immunosuppression.

Other factors that may contribute to gingivitis and/or other types of periodontal diseases include, diabetes, smoking, aging, genetic predisposition, systemic diseases and conditions, stress, inadequate nutrition, puberty, hormonal fluctuations, pregnancy, substance abuse, HIV infection, and certain medication use.

The inflammatory or swollen state is generally concomitant with a high tendency to bleeding, which results from even very low traumatic causes, such as those due to the commonly performed hygienic care of the oral cavity.

The bacteria in dental plaque irritate the gums and cause infection. When the body launches an immune response against these invaders, the gums become inflamed.

People with gingivitis usually experience little or no discomfort. Therefore, it is important to recognize the symptoms, such as gums that are red, swollen or bleed easily.

Periodontal diseases are usually treated with physical means like scaling and root planing and subsequent adjunctive therapy of localized anti-microbials.

The treatments, which are generally recommended for gingivitis, consist in the employment of special toothpastes, of mouthwashes or of liquid solutions for gums to be applied locally. None of the known products show suitable response to give a rapid and definitive solution to the problem of such diseases of paradentium, as they allow to obtain at most a temporary relief from the swollen or inflammatory state and from bleeding, and, in addition, repeated and constant applications of such products are necessary in most cases.

Several approaches to fight periodontal disease have been described in patents and in literature.

U.S. Pat. No. 6,007,795 discloses a method for inhibiting bacteria in the mouth of a patient that includes placing a particle containing a degradable material and an anti-microbial agent in the mouth of the patient. In general, the invention features a method for inhibiting bacteria in the mouth of a patient that includes placing a particle containing a degradable material and an anti-microbial agent into the mouth of a patient. The saliva in the mouth causes the degradable material in the particle to degrade, resulting in the release of the anti-microbial agent in a controlled manner over time. The exterior of the particle is water-stable allowing the particles to be incorporated into, for example, aqueous rinses or pastes without the water in the rinse or paste causing the degradable material to degrade prematurely, prior to use.

U.S. Pat. No. 5,061,106, discloses capsules or microspheres in the tuft holes in which the bristles of a toothbrush are mounted. The capsules or microspheres include a disinfectant or medicant that is released during use. A dye may also be included in the structures. The dye also is released over time to enable the user to become aware of when the contents of the capsules are depleted.

U.S. Pat. No. 5,976,506 discloses oral care products such as toothpastes with an improved sensorially-perceivable cleaning benefit. This is achieved by the inclusion in the oral care products of agglomerates, substantially free from organic and/or inorganic binding agents, whereby the agglomerates are made of at least two, chemically and/or physically different particulate materials of specified particle sizes. The inclusion of materials having a therapeutic benefit on the teeth or gums in the agglomerates such as zinc citrate provides for a further benefit in that this material is slowly released from the agglomerates, thus providing for a delivery of this material over a longer period. Upon use, the gritty-feeling agglomerates will break-down into smaller particles, thus giving the consumer the feeling of initial cleaning and subsequent polishing.

U.S. Pat. No. 4,780,320 discloses a controlled release drug delivery system for placement in the periodontal pocket. The microparticles are prepared by the solvent evaporation process and are between 10 and 500 microns in size. The matrix of the microparticles consists of cellulose acetate, ethylcellulose, polystyrene, polysulfone, polycarbonate and lacticglycolic acid copolymers.

All of these compositions, however, have proven somewhat unsatisfactory. In conventional release systems no precautions are taken in order to localize the delivery system after administration and, furthermore, the contact time in vivo between the system and a particular site is often so short that no advantages are to be expected with respect to, e.g., modifying tissue permeability.

Additionally, herb-based oral compositions for use in the treatment of diseases of oral cavity are known in the art. Moreover, herbs have been used throughout the world for treatment of many conditions and there is evidence that herbal remedies may tend to have less deleterious side effects than synthetic drugs. The term "curcuminoid substance" broadly covers the substances, e.g. curcumin, terahydrocurcumin, bishydrocurcumin, solvent extracts, crude drug, etc., obtained or derived from the plant *Curcuma longa* (*C. longa*). *C. longa*, commonly known as turmeric is a plant belonging to the family Zingiberaceae. It is commonly used as a spice in India. According to the ancient texts and traditional folklore of India, *C. longa* is also used as a medicine particularly for treating inflammatory disorders, common cold and wound healing. The rhizome and substances derived from the rhizome have been shown to possess anti-microbial, wound-healing, hypolipemic, anti-inflammatory, anti-oxidant and anti-carcinogenic properties.

Compositions, particularly oral compositions containing curcuminoid substance e.g. curcumin as an active ingredient in combination with other components have been reported in the prior art.

For instance, UK Patent Application No. GB 2317339 discloses an oral composition particularly a dentifrice composition that includes a curcuminoid, fluoride ion source as essential components in combination with one or more of an anticalculus agent, an antimicrobial agent or an antiplaque agent along with one or more carrier material which is useful for preventing and treating gingivitis, periodontitis and other diseases. The patent application also cites a prior art in the form of a Japanese Patent Application that discloses adsorbing curcumin onto a polysaccharide or a derivative of polysaccharide, protein or gel, in an oral hygiene composition, to produce a color change according to the pH of the composition as an indicator that the composition has been in mouth for a sufficient amount of time to fulfill the purpose of hygienic cleansing of the oral cavity.

USSR Inventor's Certificate No. 1132945, also cited in the above-mentioned UK Patent Application, discloses incorporating extracts of turmeric or ginger into toothpaste compositions for improved anti-inflammatory effect on tissues of the oral cavity and treatment of certain diseases of the mucous membranes of the oral cavity and marginal periodontitis.

Although the afore cited prior patent/patent applications provide compositions for oral application, these do not address the problems encountered in treating the difficult to treat diseases such as gingivitis and other periodontal diseases where the treatment requires that the composition provides a localized treatment and is resident at the site of application for longer duration. The afore cited prior art related to the compositions using curcuminoid substance suffers from the disadvantage of not providing a localized treatment that is resident for long time for the treatment of gingivitis and other periodontal diseases.

It is therefore desirable to provide a bioadhesive oral composition for the prevention and treatment of periodontal diseases such as gingivitis and periodontitis, and other periodontal diseases, wherein the contact time in vivo between the system and the site is prolonged substantially, thereby making the composition effective.

The present inventors have discovered oral compositions having improved efficacy which fulfills the long felt need for an oral composition which provides the prevention and treatment of periodontal diseases such as gingivitis and periodontitis, and other oral diseases wherein the composition of the present invention is in contact with the site for a prolonged time in order to be more efficacious. The composition of the present invention comprises a curcuminoid such as curcumin or its derivatives, analogues or curcumin extract and crude herb, and other essential excipients for enhancement of organoleptic properties.

It is therefore, an object of the invention to provide a bioadhesive composition for oral application comprising a curcuminoid substance for the prevention and treatment of gingivitis and other periodontal diseases.

Another objective of the invention is to provide a method for the treatment and prevention of gingivitis and other periodontal diseases comprising the oral application of a bioadhesive composition comprising a curcuminoid substance.

SUMMARY OF THE INVENTION

The present invention provides an oral bioadhesive composition for oral application for the treatment and prevention of gingivitis and other periodontal diseases; wherein said composition comprises:
  a. from about 0.01% to about 10% of a curcuminoid substance;
  b. one or more polymers;
  c. sodium chloride, sodium bicarbonate or mixtures thereof, and
  d. at least one pharmaceutically acceptable excipient.

Further, the present invention also provides for bioadhesive composition for oral application comprising:
  a. from about 0.01% to about 10% of a curcuminoid substance;
  b. one or more polymers;
  c. sodium chloride, sodium bicarbonate or mixtures thereof;
  d. at least one pharmaceutically acceptable excipient,
wherein the said composition exhibits a bioadhesive strength of about 1.5 to 3.5 grams.

The present invention also relates to a method for the treatment and prevention of gingivitis and other periodontal diseases using the said bioadhesive composition for oral application.

DETAILED DESCRIPTION OF THE INVENTION

The bioadhesive composition of the present invention comprises a curcuminoid substance, sodium chloride or sodium bicarbonate or mixtures thereof, one or more polymers and pharmaceutically acceptable excipients.

The term "curcuminoid substance" as used herein is intended to cover the crude drug obtained from *C. longa* and compounds and solvent extracts obtained or derived from the parts of the plant *C. longa*. The term "curcuminoid substance" is also intended to cover derivatives of the compounds isolated from the plant *C. longa*.

The term "crude drug" as used herein means the parts or the whole of the plant *C. longa* that have not been subjected to extraction with solvents. These include the powder or other size-reduced form of the rhizome of the plant *C. longa*.

The compounds obtained or derived from *C. longa* for use in this invention include curcumin, tetrahydrocurcumin, bishydrocurcumin, methylcurcumin, demethoxycurcumin, bisdemethoxycurcumin, sodium and other alkali curcuminates, p,p-dihydroxycinnamoylmethane, p-hydroxycinnamoyl(feruloyl)methane, triethylcurcumin, diacetylcurcumin and turmerones.

The curcuminoid substances suitable for use in this invention are preferably powders of the various parts of the plant, *C. longa* and compounds and solvent extracts obtained or derived from the parts of the plant, *C. longa*.

The curcuminoid substances more suitable for use in this invention are tetrahydrocurcumin, bishydrocurcumin, curcumin, and powder and solvent extracts of the rhizome of *C. longa*.

A preferred curcuminoid substance suitable for use in this invention is tetrahydrocurcumin.

Another preferred curcuminoid substance for use in this invention is curcumin.

Another preferred curcuminoid substance for use in this invention is bishydrocurcumin.

Another preferred curcuminoid substance for use in this invention is the powder of the rhizomes of *C. longa*.

A preferred extract of *C. longa* suitable for use in this invention is an ethanolic extract of the rhizomes of *C. longa* having a curcumin content of at least 95% by weight of the dried extract. An extract of this type is available commercially from Chemiloids and such extract has been used in this invention and been designated as "*C. longa* Extract (95%)" in this invention.

As used herein, the term "bioadhesion" or "bioadhesive" is intended to mean the property of the composition to adhere to the mucous membrane or to any other biological surface for a period longer than one exhibited by conventional compositions like mouthwashes and toothpowders.

As used herein, the term, "periodontal diseases" refers to those diseases, which are related to the gums and other supporting structures of the teeth.

Gingivitis is one of the mildest forms of periodontal diseases and is characterized by red, swollen and/or bleeding gums with little or no discomfort.

The other types of periodontal diseases are aggressive periodontitis, chronic periodontitis and periodontitis associated with systemic conditions like HIV, diabetes, malnutrition and immunosuppression.

As used in the specification and the appended claims, the term "about" refers to a range of value of ±10% of the specified value. For example, "about 1%" would imply "0.9 to 1.1%".

As used in the specification and the appended claims, the singular forms "a," "an," and "the" include plural referents unless the content clearly dictates otherwise.

The compositions of this invention are preferably intended to exhibit bioadhesion to the surfaces present in the oral cavity.

The bioadhesive strengths of the compositions of this invention are measured in terms of weight in grams. The bioadhesive compositions of this invention exhibit bioadhesive strength of about 1.5 to 3.5 grams.

The polymers for use in this invention are the ones that exhibit bioadhesive properties. As indicated in the examples, the polymers for use in this invention are selected from but not restricted to the group consisting of hydroxypropyl methylcellulose, hydroxypropyl cellulose, hydroxyethyl cellulose, carbomers and sodium carboxymethyl cellulose. It is to be acknowledged that many other polymers exhibiting bioadhesive properties known in the art can be used in this invention. (Ref.: *Bioadhesive Drug Delivery Systems: Fundamentals, Novel Approaches and Development*, Edited by E. Mathiowitz, Donald E. Chickering III, Claus-Michael Lehr, 1999.)

A preferred polymer for use in this invention is hydroxypropyl methylcellulose.

Another preferred polymer for use in this invention is sodium carboxymethyl cellulose.

Another preferred polymer for use in this invention is a carbomer. Carbomers are commercially available in different grades as Carbopols. One such preferred carbomer is Carbopol 934P.

The composition of the present invention comprises one or more pharmaceutically acceptable excipients.

The pharmaceutically acceptable excipients for use in this invention are selected from the group consisting of flavoring agents, diluents, sweetening agents, solubilizing agents, antioxidants, preservatives, coloring agents and buffers.

The flavoring agents that are suitable for use in this invention can be selected from among the group consisting of peppermint oil, menthol, spearmint oil, lemon oil, orange oil, cinnamon oil, limesoda and eucalyptol.

The sweetening agents that are suitable for use in this invention can be selected from among the group consisting of aspartame, saccharin sodium, sucrose, mannitol, xylitol, maltose and dextrose.

The solubilizing agents suitable for use in this invention can be selected from among the group consisting of ethanol, propylene glycol, polyethylene glycols, N-methyl pyrrolidone, 2-methoxyethanol, 2-ethoxyethanol, olive oil, castor oil, glyceryl tristearate and benzyl benzoate.

The coloring agents suitable for use in this invention are any of those approved by the regulatory authorities for oral use. Coloring agents suitable for use in this invention can be selected from the group consisting of brilliant blue, allura red, amaranth, tartrazine, titanium dioxide, iron oxide yellow, iron oxide black and iron oxide red.

The antioxidants that are suitable for use in this invention can be selected from among the group consisting of sodium bisulfite, sodium metabisulfite, sodium sulfite and ascorbic acid.

The preservatives suitable for use in this invention can be selected from among the group consisting of sodium benzoate, methyl paraben, propyl paraben and cresols. The diluents suitable for use in this invention can be selected from among the group consisting of glycerin and sorbitol solution.

The pH of the present invention is preferably adjusted to a range from about pH 6 to about pH 8 by the use of buffers. The buffers suitable for use in this invention can be selected from among the group consisting of citrate, acetate, phosphate, oxalate and amino acid buffer systems.

The present invention also relates to a method for the treatment and prevention of gingivitis and other periodontal diseases wherein said method comprises oral application of the bioadhesive composition comprising a curcuminoid substance as the active ingredient.

The amount of the bioadhesive composition is not critical, but an effective amount of the composition may be administered that is sufficient to induce a positive effect on the disease to be treated but low enough to avoid adverse effects, if any. The amount of the bioadhesive composition may vary depending on the age of the patient and the severity of the disease to be treated.

The present invention further relates to use of the bioadhesive composition for the manufacture of a medicament for the treatment and prevention of gingivitis and other periodontal diseases.

The following examples further describe and demonstrate embodiments within the scope of the present invention. These examples are given for the purpose of illustration only and may not be construed to limit the scope of the present invention.

Example 1

| Ingredient | % by weight |
|---|---|
| Tetrahydrocurcumin | 6.00 |
| Sodium bicarbonate | 0.5 |
| Sodium chloride | 0.7 |
| Polyethylene glycol 400 | 30.00 |
| Methyl paraben | 0.18 |
| Propyl paraben | 0.02 |
| Saccharin sodium | 0.40 |
| Sodium carboxymethyl cellulose (Cekol 100000) | 1 |
| Purified Water | 20 |
| Sorbitol solution 70% | QS to make 100 |

1. Sodium chloride, sodium bicarbonate and saccharin sodium were dissolved separately in portions of purified water.
2. The solutions of step 1 were mixed together with stirring to obtain a clear solution.
3. Polyethylene glycol 400 was heated to about 50°-60° C. and to it methyl paraben and propyl paraben were added slowly and mixed to get a clear solution.
4. The solution of step 3 was mixed with the solution of step 2 under stirring to obtain a uniform dispersion.
5. Sodium carboxymethyl cellulose was added to the dispersion of step 4 under stirring.

6. Tetrahydrocurcumin was added to the dispersion of step 5 in small portions under stirring to obtain a uniform dispersion.
7. The final weight of the dispersion of step 6 was made up with sorbitol solution and stirred to obtain a uniform gel.

Example 2

| Ingredient | % by weight |
| --- | --- |
| Tetrahydrocurcumin | 6.00 |
| Sodium chloride | 1.20 |
| Spearmint oil | 1.00 |
| Methyl paraben | 0.18 |
| Propyl paraben | 0.02 |
| Sodium carboxymethyl cellulose (Cekol 100000) | 3.00 |
| Saccharin sodium | 0.80 |
| Purified Water | QS to make 100 |

1. Sodium chloride, methyl paraben and propyl paraben were dissolved in a portion of purified water.
2. Saccharin sodium was dissolved in a portion of purified water.
3. The solution obtained in step 2 was added to the solution obtained in step 1 and mixed to form a solution.
4. Sodium carboxymethyl cellulose was dispersed in a portion of purified water and stirred till a uniformly thick dispersion was obtained.
5. The dispersion obtained in step 4 was added to the solution obtained in step 3 and mixed well.
6. To a portion of purified water, tetrahydrocurcumin was added and mixed well.
7. The dispersion obtained in step 6 was added to the dispersion obtained in step 5 under continuous stirring.
8. Spearmint oil was added to the dispersion of step 7.
9. The dispersion of step 8 was made up to the weight by adding purified water under stirring to obtain a uniform gel.

Example 3

| Ingredient | % by weight |
| --- | --- |
| Powder of rhizome of *C. longa* | 6.00 |
| Sodium bicarbonate | 1.00 |
| Sodium chloride | 1.50 |
| Sucrose | 20.00 |
| Methyl paraben | 0.18 |
| Propyl paraben | 0.02 |
| Sodium carboxymethyl cellulose (Cekol 50000) | 1.50 |
| Saccharin sodium | 0.20 |
| Titanium dioxide | 2.00 |
| Citric acid | 0.50 |
| Spearmint oil | 0.90 |
| Purified Water | QS to make 100 |

1. Sodium chloride, sodium bicarbonate and saccharin sodium were dissolved separately in portions of purified water.
2. The solutions of step 1 were mixed together to obtain a clear solution.
3. Portion of purified water was heated to about 50-60° C. and to it sucrose was added under stirring till clear syrup was obtained.
4. The syrup of step 3 was filtered and mixed with the solution of step 2 under stirring.
5. Citric acid was dissolved in a portion of purified water and was added to the solution of step 4 under stirring.
6. Powder of rhizome of *C. longa* was added to the solution of step 5 under stirring.
7. Sodium carboxymethyl cellulose, titanium dioxide and spearmint oil were added in small proportions to the solution of step 6 with constant stirring.
8. The final weight of the dispersion of step 7 was adjusted with purified water under stirring to obtain a uniform gel.

Example 4

| Ingredient | % by weight |
| --- | --- |
| *C. longa* Extract (95%) | 0.014 |
| Sodium bicarbonate | 1.50 |
| Sodium chloride | 1.75 |
| Sucrose | 25.00 |
| Methyl paraben | 0.18 |
| Propyl paraben | 0.02 |
| Sodium carboxymethyl cellulose (Cekol 50000) | 1.50 |
| Saccharin sodium | 0.20 |
| Titanium dioxide | 1.00 |
| Citric acid | 0.80 |
| Spearmint oil | 0.90 |
| Purified Water | QS to make 100 |

Procedure followed was same as in example 3, except for the use of *C. longa* Extract (95%) in place of powder of rhizome of *C. longa*.

Example 5

| Ingredient | % by weight |
| --- | --- |
| Powder of rhizome of *C. longa* | 0.4 |
| Sodium bicarbonate | 1.20 |
| Sodium chloride | 1.20 |
| Sucrose | 25.00 |
| Methyl paraben | 0.18 |
| Propyl paraben | 0.02 |
| Sodium carboxymethyl cellulose (Cekol 50000) | 1.50 |
| Saccharin sodium | 0.20 |
| Titanium dioxide | 1.00 |
| Citric acid | 0.80 |
| Brilliant blue | 0.0007 |
| Limesoda flavor | 0.90 |
| Purified Water | QS to make 100 |

Procedure followed was same as in example 3 with brilliant blue being added before making up the weight with purified water and limesoda flavor replacing the spearmint oil.

Example 6

| Ingredient | % by weight |
| --- | --- |
| Powder of rhizome of *C. longa* | 0.4 |
| Sodium bicarbonate | 1.0 |

-continued

| Ingredient | % by weight |
| --- | --- |
| Sodium Chloride | 1.75 |
| Sucrose | 25.00 |
| Methyl paraben | 0.18 |
| Propyl paraben | 0.02 |
| Sodium carboxymethyl cellulose (Cekol 50000) | 1.50 |
| Saccharin sodium | 0.20 |
| Titanium dioxide | 1.00 |
| Citric acid | 0.80 |
| Brilliant blue | 0.0007 |
| Limesoda flavor | 0.90 |
| Purified Water | QS to make 100 |

Procedure followed was same as in example 3 with brilliant blue being added before making up the weight with purified water and limesoda flavor replacing the spearmint oil.

Example 7

| Ingredient | % by weight |
| --- | --- |
| C. longa Extract (95%) | 0.016 |
| Sodium bicarbonate | 0.50 |
| Sodium chloride | 1.00 |
| Sucrose | 25.00 |
| Methyl paraben | 0.18 |
| Propyl paraben | 0.02 |
| Sodium carboxymethyl cellulose (Cekol 50000) | 1.50 |
| Saccharin sodium | 0.20 |
| Titanium dioxide | 1.00 |
| Citric acid | 0.80 |
| Brilliant blue | 0.0006 |
| Spearmint oil | 0.90 |
| Purified Water | QS to make 100 |

Procedure followed was same as in example 3, except for the use of C. longa Extract (95%) in place of powder of rhizome of C. longa and the addition of brilliant blue before finally making up the weight with purified water.

Example 8

| Ingredient | % by weight |
| --- | --- |
| C. longa Extract (95%) | 0.016 |
| Sodium bicarbonate | 1.20 |
| Sodium chloride | 1.20 |
| Sucrose | 25.00 |
| Methyl paraben | 0.18 |
| Propyl paraben | 0.02 |
| Sodium carboxymethyl cellulose (Cekol 50000) | 1.50 |
| Saccharin sodium | 0.20 |
| Titanium dioxide | 1.00 |
| Citric acid | 0.80 |
| Sodium citrate | 0.50 |
| Sodium metabisulfite | 0.08 |
| Brilliant blue | 0.0003 |
| Spearmint oil | 0.90 |
| Purified Water | QS to make 100 |

Procedure followed was same as in example 3, except for the use of C. longa extract (95%) in place of powder of rhizome of C. longa and the addition of sodium metabisulfite and sodium citrate before finally making up the weight with purified water.

Example 9

| Ingredient | % by weight |
| --- | --- |
| C. longa Extract (95%) | 1.3 |
| Sodium bicarbonate | 0.50 |
| Sodium chloride | 1.00 |
| Sucrose | 25.00 |
| Methyl paraben | 0.18 |
| Propyl paraben | 0.02 |
| Sodium carboxymethyl cellulose (Cekol 50000) | 1.50 |
| Saccharin sodium | 0.20 |
| Titanium dioxide | 2.40 |
| Citric acid | 0.80-1.0 |
| Sodium citrate | 0.80-1.0 |
| Sodium metabisulfite | 0.10 |
| Brilliant blue | 0.00176 |
| Limesoda flavor | 1.20 |
| Purified Water | QS to make 100 |

Procedure followed was same as in example 3, except for the use of C. longa extract (95%) in place of powder of rhizome of C. longa, the use of limesoda flavor in place of spearmint oil and the addition of sodium metabisulfite, brilliant blue and sodium citrate before finally making up the weight with purified water.

Example 10

| Ingredient | % by weight |
| --- | --- |
| C. longa Extract (95%) | 1.3 |
| Sodium chloride | 1.00 |
| Methyl paraben | 0.18 |
| Propyl paraben | 0.02 |
| Carbopol 934P | 1.0 |
| Polyethylene glycol 400 (PEG 400) | 10.00 |
| Pemulen TR-2 | 0.30 |
| Span 80 | 0.20 |
| Saccharin sodium | 0.30 |
| Citric acid | 1.00 |
| Sodium metabisulfite | 0.10 |
| Brilliant blue | 0.0033 |
| Limesoda flavor | 1.50 |
| Purified Water | QS to make 100 |

1. C. longa Extract (95%) and Pemulen TR-2 were dissolved in a portion of polyethylene glycol 400 under stirring and heated to about 50° C.
2. Span 80 was added to purified water under stirring and heated to about 50° C.
3. The solution of step 1 was added to the solution of step 2, maintaining the temperature of 50° C. and mixed under stirring.
4. Saccharin sodium and sodium metabisulfite were dissolved in a portion of purified water.
5. Methyl paraben and propyl paraben were dissolved in a portion of polyethylene glycol 400.
6. The solution of step 5 was added to the solution of step 4 and mixed under stirring.
7. Sodium chloride, citric acid and brilliant blue were added to the mixture obtained in step 6 under stirring.

8. To the dispersion obtained in step 7, Carbopol 934P was added in small proportions under stirring and subsequently titanium dioxide was added in small proportions under stirring.
9. Limesoda flavor was added to the dispersion obtained in step 8 and the weight was made up with purified water and mixed thoroughly to obtain a uniform gel.

Example 11

| Ingredient | % by weight |
| --- | --- |
| *C. longa* Extract (95%) | 1.3 |
| Sodium bicarbonate | 0.50 |
| Sodium chloride | 0.50 |
| Sucrose | 20.00 |
| Methyl paraben | 0.18 |
| Propyl paraben | 0.02 |
| Sodium carboxymethyl cellulose (Cekol 50000) | 1.00 |
| Propylene glycol | 2.50 |
| Hydroxypropyl methylcellulose (100 LV) | 10.00 |
| Saccharin sodium | 0.20 |
| Citric acid | 1.60 |
| Sodium metabisulfite | 0.10 |
| Purified Water | QS to make 100 |

1. *C. longa* Extract (95%) was dispersed in a portion of purified water under stirring.
2. A portion of purified water was heated to 60° C. Methyl paraben, propyl paraben and sucrose were added to this heated purified water and stirred to obtain a clear solution.
3. Sodium bicarbonate and sodium chloride were dissolved in a small portion of purified water.
4. The solution of step 3 was added to the solution of step 2 and mixed well under stirring.
5. Saccharin sodium, citric acid and sodium metabisulfite were dissolved separately in portions of purified water.
6. The solutions of step 5 were added to the solution of step 4 and mixed well under stirring.
7. Sodium carboxymethyl cellulose was dispersed in a portion of purified water and kept under stirring for about one hour.
8. The dispersion of step 7 was added to the solution of step 6 under stirring.
9. Hydroxypropyl methylcellulose was dispersed in propylene glycol.
10. The dispersion of step 9 was added to the dispersion of step 8 under stirring.
11. The dispersion of step 1 was added to the dispersion of step 10 and mixed well under stirring. The weight was made up with purified water and mixed to obtain a uniform gel.

Experiment 12

| Ingredient | % by weight |
| --- | --- |
| *C. longa* Extract (95%) | 1.3 |
| Sodium chloride | 1.5 |
| Sodium bicarbonate | 1.2 |
| Methyl paraben | 0.18 |
| Propyl paraben | 0.02 |
| Hydroxypropyl cellulose (Klucel HXF) | 3.0 |
| Polyethylene glycol 400 | 70.00 |
| Glycerin | 4.00 |
| Saccharin sodium | 0.20 |
| Citric acid | 1.60 |
| Sodium metabisulfite | 0.10 |
| Purified Water | QS to make 100 |

1. *C. longa* Extract (95%) was dissolved in a portion of polyethylene glycol 400.
2. Methyl paraben and propyl paraben were dissolved in a portion of polyethylene glycol 400.
3. The solutions of step 1 and 2 were mixed well under stirring to obtain a uniform solution.
4. Sodium bicarbonate, sodium chloride were dissolved in a portion of purified water.
5. Sodium citrate and sodium metabisulfite were dissolved in a portion of purified water.
6. The solutions obtained in step 4 and 5 were added to the solution obtained in step 3 and mixed well to obtain a uniform dispersion. Glycerin was added to the thus obtained dispersion under stirring.
7. To the dispersion of step 6, hydroxypropyl cellulose was added in small proportions under stirring to obtain a uniform dispersion.
8. Saccharin sodium and citric acid were dissolved in a portion of purified water and added to the dispersion obtained in step 7 under stirring.
9. Final weight was made up with purified water and the dispersion was mixed well to obtain a uniform gel.

Experiment 13

| Ingredient | % by weight |
| --- | --- |
| *C. longa* Extract (95%) | 1.3 |
| Sodium bicarbonate | 1.50 |
| Sodium chloride | 1.50 |
| Methyl paraben | 0.18 |
| Propyl paraben | 0.02 |
| Hydroxypropyl cellulose (Klucel HXF) | 2.00 |
| N-methyl pyrrolidone (Pharmasolve) | 27.00 |
| Polyoxyl 40 Hydrogenated Castor Oil (Cremophor RH40) | 2.00 |
| Saccharin sodium | 0.20 |
| Citric acid | 2.40 |
| Purified Water | QS to make 100 |

1. *C. longa* Extract (95%) was dissolved in N-methyl pyrrolidone.
2. Polyoxyl 40 hydrogenated castor oil, methyl paraben and propyl paraben were dissolved in a portion of purified water.
3. Sodium chloride and sodium bicarbonate were dissolved in a portion of purified water.
4. The solution of step 3 was added to the solution of step 2 and mixed well.
5. Saccharin sodium and citric acid were dissolved in a portion of purified water.
6. The solution of step 5 was added to the solution of step 4.
7. To the solution of step 6, hydroxypropyl cellulose was added in small portions under continuous stirring to obtain a homogenous dispersion.

8. To the dispersion of step 7, the solution of step 1 was added with stirring.
9. The weight of the dispersion of step 8 was made up with purified water and stirred to obtain a uniform gel.

Example 14

Determination of Bioadhesive Strength

Bioadhesive strength was estimated in terms of weight. Apparatus used was a two pan weighing balance that has been modified wherein one pan was removed and replaced with a flat faced tablet punch. The tablet punch was coated with 5% sodium carboxymethyl cellulose. The composition of the present invention was allowed to be in contact with the pre-coated tablet punch for about 3-4 minutes. The balance was then moved from the resting position and fractional weights were placed slowly on the pan. The point at which the contact between the tablet punch and the composition breaks was recorded as the bioadhesive strength, which is expressed in grams.

| Sr. No. | Example No. | Bioadhesive Strength (grams) |
| --- | --- | --- |
| 1 | 2 | 1.85 |
| 2 | 3 | 1.55 |
| 3 | 5 | 2.0 |
| 4 | 8 | 2.35 |
| 5 | 9 | 2.40 |
| 6 | 11 | 1.65 |
| 7 | 13 | 1.70 |

We claim:

1. A bioadhesive composition for application at surfaces of the oral cavity of a patient for treating periodontal diseases consisting essentially of:
   a. 0.01% to 10% of a *Curcuma longa* extract,
   b. one or more polymers in an amount of 1 to 3%,
   c. sodium chloride, sodium bicarbonate or mixtures thereof, and
   at least one additional pharmaceutically acceptable excipient, wherein said bioadhesive composition is an oral gel which exhibits a bioadhesive strength of about 1.5 to about 3.5 grams, wherein the polymer is selected from the group consisting of hydroxypropyl cellulose, hydroxypropyl methylcellulose, sodium carboxymethylcellulose, hydroxyethyl cellulose and carbomers.

2. The bioadhesive composition according to claim 1, wherein said composition comprises up to 2% of sodium chloride by weight of the composition.

3. The bioadhesive composition according to claim 1, wherein said composition comprises up to 2% of sodium bicarbonate by weight of the composition.

4. A method for treating a periondontal disease in a patient in need thereof, consisting essentially of administering by oral application to said patient a therapeutically effective amount of the bioadhesive composition as claimed in claim 1.

5. The method according to claim 4, wherein the disease is gingivitis.

6. A bioadhesive composition for application at surfaces of the oral cavity of a patient for treating periodontal diseases consisting of:
   a. 0.01% to 10% of a *Curcuma longa* extract,
   b. one or more polymers in an amount of 1 to 3%,
   c. sodium chloride, sodium bicarbonate or mixtures thereof, and
   at least one additional pharmaceutically acceptable excipient, wherein said bioadhesive composition is an oral gel which exhibits a bioadhesive strength of about 1.5 to about 3.5 grams, wherein the polymer is selected from the group consisting of hydroxypropyl cellulose, hydroxypropyl methylcellulose, sodium carboxymethylcellulose, hydroxyethyl cellulose and carbomers.

7. The bioadhesive composition of claim 1, wherein the extract is a powder or solvent extract.

* * * * *